United States Patent [19]

Lerch

[11] Patent Number: 4,659,838
[45] Date of Patent: Apr. 21, 1987

[54] METHOD OF RESOLVING BICYCLIC IMINO-α-CARBOXYLIC ACID ESTER RACEMATES

[75] Inventor: Ulrich Lerch, Hofheim am Taunus, Fed. Rep. of Germany

[73] Assignee: Hoechst Aktiengesellschaft, Fed. Rep. of Germany

[21] Appl. No.: 681,329

[22] Filed: Dec. 13, 1984

[30] Foreign Application Priority Data

Dec. 15, 1983 [DE] Fed. Rep. of Germany ....... 3345355

[51] Int. Cl.[4] .................. C07D 209/12; C07D 209/52
[52] U.S. Cl. .................................... 548/452; 548/515; 548/535
[58] Field of Search ........................ 548/515, 452, 535

[56] References Cited

U.S. PATENT DOCUMENTS 3,880,866  4/1975  Herbst et al. .......................... 546/64
4,111,951  9/1978  Hengartner ........................... 548/535
4,255,334  3/1981  Day et al. ............................. 548/515
4,344,949  8/1982  Hoefle et al. .................... 546/142 X

FOREIGN PATENT DOCUMENTS 0115345   8/1984  European Pat. Off. .
50-101355 8/1975  Japan .................................. 548/535
573480   10/1977  U.S.S.R. ............................. 548/535

OTHER PUBLICATIONS

Greenstein & Winitz, "Chemistry of the Amino Acids", New York (1961), pp. 716–717.

Primary Examiner—Joseph Paul Brust

Attorney, Agent, or Firm—Finnegan, Henderson, Farabow, Garrett & Dunner

[57] ABSTRACT

The invention relates to a process for resolving racemic mixtures of bicyclic imino-α-carboxylic acid esters into the components of the formula Ia and Ib

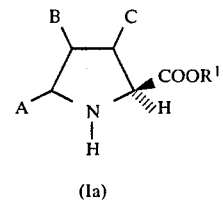 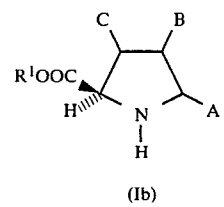

(Ia) (Ib)

in which
R[1] stands for an aliphatic, cycloaliphatic, aromatic or araliphatic radical,
A denotes hydrogen and B and C together form a carbon chain or C denotes hydrogen and A and B together form a carbon chain, by crystallizing diastereoisomeric salts, which comprises preparing the salts of the racemic esters with optically active O,O-diacyltartaric acids in a suitable solvent in which only one of the two diastereoisomeric salts crystallizes in optically pure form, if desired purifying the diastereoisomeric salt by recrystallization, reprecipitation or trituration, and finally adding basec to the salt to cleave it into the pure enantiomer of the formula Ia or Ib.

The invention also relates to diastereoisomeric salts of an ester of the formula Ia or Ib and a diacyltartaric acid.

20 Claims, No Drawings

METHOD OF RESOLVING BICYCLIC IMINO-α-CARBOXYLIC ACID ESTER RACEMATES

The clean and quantitative separation of a racemate into its components by crystallizing a diastereoisomeric salt represents an ideal which is rarely realized, if ever. It normally requires extensive fractional crystallizations which are associated not only with a great deal of work but, frequently, also with appreciable amounts of lost substance. It is impossible to make a priori predictions about which specific conditions should be employed for successfully resolving a particular racemate, so that the question of which optically active auxiliary substance should be used and the suitable solvent remains undecided in every case (cf. in this context J. P. Greenstein and M. Winitz, "Chemistry of the Amino Acids", New York (1961), pages 716 and 717).

A method for resolving racemates of bicyclic imino-α-carboxylic acid esters has already been proposed (EP-A-115,345). In this method, diastereoisomeric salts of these compounds, with N-acylated, optically active amino acids, such as, for example, N-benzyloxycarbonyl-S-phenylalanin, are prepared and separated by fractional crystallization.

It has been found, surprisingly, that O,O-diacyltartaric acids are likewise highly suitable for separating bicyclic imino-α-carboxylic acids into the optical antipodes.

The invention thus relates to a method for separating racemic mixtures of bicyclic imino-α-carboxylic acid esters into the components of the formula Ia and Ib

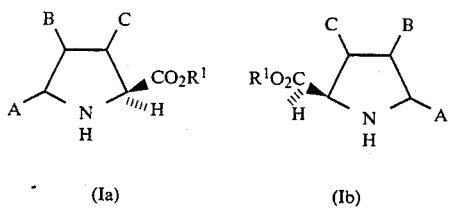

(Ia)        (Ib)

in which $R^1$ stands for an aliphatic radical of 1 to 6 carbon atoms, a cycloaliphatic radical of 4 to 10 carbon atoms, an aromatic radical of 6 to 12 carbon atoms or an araliphatic radical of 7 to 15 carbon atoms, (a) A denotes hydrogen and B and C together form a chain of the formula $-[CH_2]_n-$ with n=3, 4, 5 or 6 or a chain of the formula $-[CH_2]_p-CH=CH-[CH_2]_q-$ with (p+q)=1, 2, 3 or 4 or (b) C denotes hydrogen and A and B together form one of the chains defined above under (a), which comprises preparing the salts of said racemic esters I with optically active O,O-diacyltartaric acid II

in which $R^2$ denotes acyl, in a suitable solvent in which only one of the two diastereoisomeric salts crystallizes out, if desired further purifying this salt by decrystallization, reprecipitation or trituration, and finally cleaving the optically uniform salt into the components by adding base to obtain one of the two antipodes Ia or Ib in pure form. The mother liquor obtained on separating off the less soluble diastereoisomeric salt can be made to yield the more soluble diastereoisomeric salt and hence the second antipode of I. Preferred acyl radicals $R^2$ are lower alkanoyl and ($C_7$ to $C_{11}$)-aroyl, in particular ($C_1$ to $C_6$)-alkyl and benzoyl. The method is preferably applied to racemic mixtures of compounds of the formulae Ia+Ib in which A and B each denote $-[CH_2]_3-$ or $-[CH_2]_4-$ and C denotes hydrogen. The cis-endo configuration of these compounds is also preferable.

The optically uniform bicyclic imino-α-carboxylic acid esters can be used, for example, as starting materials in the synthesis of optically pure angiotensin converting enzyme inhibitors. Compounds of this type are known, for example from EP-A-50,800, EP-A-49,658, EP-A-46,953, EP-A-79,022 and U.S. Pat. No. 4,344,949; they can be used for treating high blood pressure.

Compared with the process proposed in EP-A-115,345, the process according to the invention has the advantage that the diacyltartaric acids used as auxiliary substance are much more economical than the N-acyl derivatives of optically active R- or S-amino acids required there, no recrystallization is required, and the yields of optically uniform antipodes Ia or Ib are higher. Even the chemical purity of the antipodes Ia or Ib obtained in the process according to the invention is higher.

In the process according to the invention, first of all the racemic compounds of the formula Ia+Ib are liberated from their salts with inorganic acids. This is done by using a two-phase system comprising dilute sodium hydroxide solution and preferably an ether, such as, for example, diisopropyl ether or tert.-butyl methyl ether. The salt is preferably stirred in this mixture at temperatures between 0° and 20°, and the phases are separated until everything has dissolved. After the organic phase has been washed with water and the aqueous phase has been extracted with the corresponding ether, the organic phase is evaporated to dryness, giving the free racemic compound 1 in high purity and high yield (96–99%). Moreover, the phase separation does not give rise to problems due to emulsification, as is the case, for example, with the use of methylene chloride.

The diastereoisomeric diacyltartrates are prepared by reacting the racemic bicyclic imino-α-carboxylic acid esters of the formula Ia+Ib with optically active O,O-diacyltartaric acids of the formula II. In this reaction the diacyltartaric acid is used in an amount of 0.5 to 1.5 mol, preferably 0.9–1.1 mol.

The preferred solvent for the formation of the diastereoisomeric diacyltartrates is a solvent from which one of the two diastereoisomeric salts crystallizes out while the other remains in solution. Preference is given here to the lower esters, such as ethyl acetate, ketones, such as acetone or 2-butanone, ethers, such as tetrahydrofuran, 1,2-dimethoxyethane or dioxane, low molecular weight alcohols, such as methanol, ethanol or isopropanol, nitriles, such as acetonitrile, and halogenated hydrocarbons, such as, for example, methylene chloride. These solvents, in particular ethyl acetate, can be used alone, but they are preferably used in the form of mixtures with solvents of low polarity in which the diacyltartrates of compounds of the formula I are less soluble, for example higher esters such as butyl acetate, aromatics such as toluene, polar ethers such as diethyl ether, diisopropyl ether or tert.-butyl methyl ether, or hydrocarbons such as cyclohexane, hexane or petroleum ether.

The solvent for the formation of the diastereoisomeric salts of Ia or Ib and II is particularly preferably ethyl acetate, acetone or 2-butanone, if desired together with tert.-butyl methyl ether, diisopropyl ether or butyl acetate. The range of possible reaction temperatures extends from $-20°$ to $+50°$ C., but the preferred temperatures range from $-5°$ to $+30°$ C.

In a preferred embodiment of the process according to the invention, the ester of the racemic bicyclic imino-α-carboxylic acid of the formulae Ia+Ib is added to a solution of O,O-dibenzoyl-L-tartaric acid in acetone, ethyl acetate or 2-butanone, if necessary the mixture is seeded with the product, and an accurately determined amount of, for example, tert.-butyl methyl ether is then added in accordance with a defined dosing schedule. Stirring takes place first of all at room temperature and then at temperatures between $-5°$ and $+5°$ C. Removal of the mother liquor and a thorough wash then produces the diastereoisomeric salt in yields of 80–100%.

The isolated diastereoisomeric salts of the process according to the invention are generally obtained in a sufficiently optically pure form that they can be cleaved directly, i.e. without further purification.

Yet should it be necessary to purify the salt further, this can be done by recrystallization, reprecipitation or trituration. In essence these operations are carried out in similar solvents or solvent mixtures as used for preparing the diastereoisomeric salts.

For instance, the salt can be recrystallized by dissolving it in hot acetone or 2-butanone and allowing the solution to cool down while stirring and seeding it, in the absence or presence of an apolar solvent, such as, for example, tert.-butyl methyl ether, diisopropyl ether or butyl acetate, chilling, and isolating the purified salt by filtration.

Another way (reprecipitation) comprises dissolving the diastereoisomeric salt in the absence of heat at room temperature in a small amount of a solvent in which the salt is readily soluble, such as, for example, a low molecular weight alcohol, and then initiating the crystallization of the salt by adding a less polar solvent or solvent mixture, such as, for example, ethyl acetate/tert.-butyl methyl ether.

It is finally also possible to employ the method of trituration which involves stirring the crude diastereoisomeric salt in a suitable solvent, such as, for example, ethyl acetate, or a solvent mixture, such as, for example, 2-butanone/tert.-butyl methyl ether, at room temperature and then allowing the suspension to cool down and filtering it.

To cleave the optically pure diastereoisomeric salts, a base in water is added, and the optically active compound Ia or Ib is taken up in a solvent which is immiscible with water.

Examples of particularly suitable bases are alkali metal hydroxides such as sodium hydroxide, potassium hydroxide or lithium hydroxide.

The organic solvents used in the process according to the invention are such that addition of an inorganic acid thereto directly yields the salt of the optically pure compound Ia or Ib with that acid in the form of a precipitate, which can be isolated by filtration. Examples of suitable solvents are ethers such as diisopropyl ether or tert.-butyl methyl ether, hydrocarbons such as petroleum ether or toluene, methylene chloride and ethyl acetate.

The salt is preferably cleaved at $-5°$ to $+30°$ C.; the temperatures are particularly preferably between 0° and 20° C. in order to suppress the hydrolysis of the ester function.

The preferred procedure for cleaving the optically pure salt is in detail as follows: the salt is suspended in one of the abovementioned solvents, preferably in diisopropyl ether, tert.-butyl methyl ether or toluene, and a solution of 2-3 times the molar amount of sodium hydroxide in water is added at 0°-20° C. with stirring. The mixture is stirred until the crystals have completely dissolved, and the phases are separated. The optically pure imino-α-carboxylic acid ester of the formula Ia or Ib can be isolated by evaporating the organic solvent or, advantageously, be precipitated in the form of a salt by adding an inorganic acid, such as, for example, hydrogen chloride in gas form or other solution, or sulfuric acid. The compounds of the formulae Ia and Ib are stable in salt form. The process according to the invention produces the salts of the optically pure compounds Ia and Ib with mineral acid in yields of 75–90% based on the racemic compound hydrochlorides used as the starting material. The products are distinguished by high chemical and optical purity.

EXAMPLE 1

(A) Racemic benzyl cis-endo-2-azabicyclo[3.3.0]octane-3-carboxylate 56.4 g (0.2 mol) of racemic benzoyl cis-endo-2-azabicyclo[3.3.0]octane-3-carboxylate hydrochloride are suspended in 250 ml of tert.-butyl methyl ether, and a solution of 8.8 g (0.22 mol) of NaOH in 90 ml of water is added with vigorous stirring at an internal temperature of 0°-5° C. As soon as everything has gone into solution (after about 15 minutes), the phases are separated. The aqueous phase is extracted twice with 30 ml of tert.-butyl methyl ether each time and is discarded. The combined organic phases are washed twice with 30 ml of water each time and are dried over anhydrous sodium sulfate. Concentrating under reduced pressure and in the end under a high vacuum produces 47.5–48.5 g of an almost colorless oil (96.8–98.8%).

(B) Dibenzoyltartrate of benzyl cis-endo-azabicyclo[3.3.0]octane-3-(S)-carboxylate 37.7 g (0.1 mol) of dibenzoyl-L-tartaric acid hydrate are dissolved at room temperature in 60 ml of 2-butanone. 24.6 g (0.1 mol) of racemic benzyl cis-endo-2-azabicyclo[3.3.0]octane-3-carboxylate in 40 ml of 2-butanone are added at an internal temperature of 10°-15° C. (exothermic reaction), and the mixture is seeded with about 0.2 g of the dibenzoyltartrate. The mixture is vigorously stirred at the abovementioned temperature for 30 minutes until a thick, colorless paste is formed (about 30 minutes). The paste is then cooled down to an internal temperature of 0° C., is stirred at this temperature for 30 minutes, and is then allowed to flow into a mixture of 100 ml of tert.-butyl methyl ether in 25 ml of 2-butanone in the course of 30 minutes during which an internal temperature of 0° C. is maintained. The mixture is stirred at this temperature for an additional hour and is filtered with suction, and the filter cake is washed carefully twice with 20 ml of a 1:1 mixture of tert.-butyl methyl ether and 2-butanone each time. Drying leaves 27.0 g (89.5% ≙ 88.3% based on the racemic hydrochloride) of the desired salt of melting point 108°-109° C., $[\alpha]_D^{20} = -87.7°$ (c=1, CH$_3$OH).

(C) Benzyl cis-endo-2-azabicyclo[3.3.0]octane-3-(S)-carboxylate hydrochloride 18.11 g (30 mmol) of the unpurified dibenzoyltartrate prepared in Example 1B are vigorously stirred with 75 ml of diisopropyl ether until the crystalline lumps have largely disintegrated and a smooth paste is formed. A solution of 3.0 g (75 mmol) of NaOH in 50 ml of water is added at temperatures below 15° C., and the mixture is thoroughly stirred until virtually everything has gone into solution. The phases are separated, the aqueous phase is extracted twice with 10 ml of diisopropyl ether each time, the combined organic phases are washed twice with 10 ml of water each time, are dried over sodium sulfate and are seeded with a little hydrochloride of the optically active benzyl ester, and hydrochloric acid in ether solution is gradually added with stirring until the mixture shows a marked acid reaction. The colorless hydrochloride is filtered off with suction after 10 minutes of stirring and is washed twice with 10 ml of diisopropyl ether each time. Drying leaves 8.1 g (95.8%) of colorless crystals. Melting point 183°-185° C.

$[\alpha]_D^{20} = -32.7°$ (c=1, CH$_3$OH); $-38.4°$ (c=1, H$_2$O).

Total yield based on starting hydrochloride of racemic benzyl cis-endo-2-azabicyclo[3.3.0]octane-3-carboxylate: 84.6%.

EXAMPLE 2

A. Dibenzoyltartrate of benzyl (S)-azabicyclo[3.3.0]octane-3-carboxylate 1. 15.1 g (0.04 mol) of dibenzoyl-L-tartaric acid hydrate are dissolved at room temperature in 50 ml of ethyl acetate, and 9.82 g (0.04 mol) of racemic benzyl cis-endo-2-azabicyclo[3.3.0]octane-3-carboxylate are added at an internal temperature of 15°-20° C. The mixture is seeded with about 0.1 g of the dibenzoyltartrate, is stirred at the abovementioned temperature for 15-30 minutes until a thick paste is formed, and is then cooled down to an internal temperature of 0° C. 15 minutes after this temperature has been reached a mixture of 40 ml of ethyl acetate and 8 ml of tert.-butyl methyl ether is slowly added dropwise in the course of 15 minutes. The mixture is then stirred at 0° C. for a further hour, and the pale yellow suspended matter is filtered off with suction, is washed twice with a mixture of 9 ml of ethyl acetate and 1 ml of tert.-butyl methyl ether each time, and is dried at room temperature. This gives 12.1 g (100%) of slightly yellowish crystals of melting point 104°-108° C. $[\alpha]_D^{20} = -84.7°$ (c=1, CH$_3$OH).

2. 10 g of the crude dibenzoyltartrate obtained are stirred at room temperature in 30 ml of 2-butanone for 30 minutes. 30 ml of tert.-butyl methyl ether are then added in the course of 15 minutes, and the mixture is stirred at room temperature for 1 hour and then at 0° C. for 1 hour, and is filtered with suction. The filter cake is washed twice with 8 ml of a 4:6 mixture of 2-butanone/tert.-butyl methyl ether each time. Drying leaves 8.7 g of colorless crystals (87% of theory based on racemic benzyl cis-endo-2-azabicyclo[3.3.0]octane-3-carboxylate). Melting point 106°-108°, $[\alpha]_D^{20} = -88.3°$ (c=1, CH$_3$OH).

(B) Benzyl cis-endo-2-azabicyclo[3.3.0]octane-3-(S)-carboxylate hydrochloride The dibenzoyltartrate prepared in Example 2 A2 was turned by the method described in Example 1c into the hydrochloride of benzyl cis-endo-2-azabicyclo[3.3.0]octane-3-(S)-carboxylate. Melting point 184°-185.5° C.

$[\alpha]_D^{20} = -32.5°$ (c=1, CH$_3$OH); $-37.1°$ (c=1, H$_2$O).

Total yield based on starting racemic hydrochloride: 79.2% of theory.

EXAMPLE 3

(A) Recrystallization of the crude dibenzoyltartrate of benzyl cis-endo-2-azabicyclo[3.3.0]octane-3-(S)-carboxylate 15 g of the crude dibenzoyltartrate prepared in Exampl 1 B are rapidly dissolved in 45 ml of preheated 2-butanone at 60°-65° C., and 40 ml of tert.-butyl methyl ether are immediately added without further heating, which should have the effect of reducing the temperature to about 35°-40° C. Feed crystals are added, the mixture is cooled down to 20° C. and is stirred at this temperature for 30 minutes, a further 40 ml of tert.-butyl methyl ether are then added in the course of 10 minutes, and the mixture is finally stirred at 0° C. for 1 hour. This produces 13.4 g (89.3%) of colorless crystals of melting point 110°-112° C. $[\alpha]_D^{20} = -87.1°$ (c=1, CH$_3$OH).

(B) Benzyl cis-endo-2-azabicyclo[3.3.0]octane-3-(S)-carboxylate hydrochloride The same method as described in Example 1 C was used to prepare the hydrochloride from the reprecipitated dibenzoyltartrate in 93.7% of theory. Melting point 191°-192° C. $[\alpha]_D^{20} = -33.8°$ (C=1, CH$_3$OH); $-39.6°$ (C=1, H$_2$O).

Total yield based on starting racemic hydrochloride=73.3%.

I claim:

1. A process for resolving racemic mixtures of bicyclic imino-$\alpha$-carboxylic acid esters into the components of formulae Ia' and Ib'

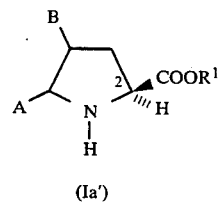
(Ia')

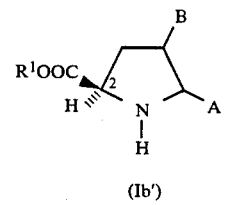
(Ib')

in which the carbon atom in the 2-position is in the S configuration in formula Ia' or in the R configuration in formula Ib', and in which R$^1$ stands for alkyl of 1 to 6 carbon atoms, cycloalkyl of 4 to 8 carbon atoms or aralkyl of 7 to 13 carbon atoms and A and B together form a chain of the formula $-(CH_2)_n-$ wherein n is 3, 4, 5 or 6, or a chain of the formula $-(CH_2)_p-CH=CH-(CH_2)_q-$ wherein (p+q) is 1, 2, 3 or 4 by crystallizing diastereoisomeric salts, which process comprises preparing the salts of the racemic mixture of compounds of formulae Ia' and Ib' with optically active O,O-diacyltartaric acids of formula II

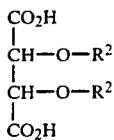

(II)

in which R² denotes aroyl of 7 to 11 carbon atoms, in an ester, a ketone, an ether, a lower alcohol, a nitrile or a halogenated hydrocarbon as a solvent, or in a mixture of two or more solvents selected from the group consisting of esters, ketones, ethers, lower alcohols, nitriles and halogenated hydrocarbons, and
  (a) cleaving the salt into the pure enantiomer of formula Ia' or Ib' by adding a base, or
  (b) purifying the diastereoisomeric salt by recrystallization, reprecipitation or trituration, and cleaving the salt into the pure enantiomer of formula Ia' or Ib' by adding a base.

2. The process as claimed in claim 1, wherein the salts of esters of formulae Ia' and Ib' in which the two bridgehead hydrogen atoms are in the cis configuration and the COOR group is oriented in the endo-position relative to the bicyclic ring system are prepared with acids of formula II and crystallized.

3. The process as claimed in claim 1, wherein A and B together stand for $-(CH_2)_n-$ wherein n is 3 or 4.

4. The process according to claim 1, wherein the diastereoisomeric salts are prepared in a solvent mixture.

5. The process as claimed in claim 4, wherein the solvent mixture used contains one or more less polar solvents.

6. The process as claimed in claim 1, wherein the solvent used in the preparation of the diastereoisomeric salts is ethyl acetate, 2-butanone or acetone.

7. The process as claimed in claim 6, wherein the diastereoisomeric salt is purified by recrystallization, reprecipitation or trituration in the same solvent which was used for its preparation.

8. The process as claimed in claim 6, wherein the diastereoisomeric salt obtained is purified by recrystallization, reprecipitation or trituration in the same solvent mixture which was used for its preparation.

9. The process as claimed in claim 1, wherein the solvent used in the liberation of the racemic imino-α-carboxylic acid esters of formulae Ia' and Ib' from their salts with inorganic acids is tert.-butyl methyl ether or diisopropyl ether.

10. The process as claimed in claim 1, wherein the crystalline diastereoisomeric salt is cleaved without further purification.

11. The process as claimed in claim 1, wherein the diastereoisomeric salts of compounds of formula Ia' or Ib' with compounds of formula II are cleaved by means of an aqueous alkali metal hydroxide and the optically pure bases of formula Ia' or Ib' are taken up in an organic solvent which is immiscible with water.

12. The process as claimed in claim 11, wherein an inorganic acid is used to precipitate the optically pure bases directly from the organic solvent in salt form, and the salts are isolated.

13. The process as claimed in claim 1, wherein the enantiomer of formula Ia' or Ib' is converted into a salt with a mineral acid.

14. The process as claimed in claim 1, wherein the solvent used in the preparation of the diastereoisomeric salts is ethyl acetate, 2-butanone or acetone, combined with a less polar solvent.

15. The process as claimed in claim 14, wherein the less polar solvent is selected from the group consisting of tert.-butyl methyl ether, diisopropyl ether, toluene or butyl acetate.

16. A diastereoisomeric salt of a bicyclic imino-α-carboxylic acid ester of formula Ia' or Ib' as set forth in claim 1 in which A, B, R¹, n, p and q, and the configurations of the carbon atoms in the 2-position are as defined in claim 1, with an optically active O,O-diacyltartaric acid of formula II.

17. A diastereoisomeric salt as claimed in claim 16, wherein n is 3 or 4.

18. A diastereoisomeric salt as claimed in claim 17, wherein the compound of formula Ia' or Ib' has the cis configuration at the two bridgehead hydrogen atoms and the COOR¹ group is oriented in the endo-position relative to the bicyclic ring system.

19. A diastereoisomeric salt as claimed in claim 16, wherein R² stands for benzoyl.

20. A diastereoisomeric salt as claimed in claim 16, wherein R¹ stands for benzyl or tert.-butyl.

* * * * *